(12) United States Patent
Fukai et al.

(10) Patent No.: US 7,424,093 B2
(45) Date of Patent: Sep. 9, 2008

(54) FLUORESCENT X-RAY ANALYSIS APPARATUS

(75) Inventors: Takayuki Fukai, Chiba (JP); Yoshiki Matoba, Chiba (JP); Masanori Takahashi, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 11/805,665

(22) Filed: May 24, 2007

(65) Prior Publication Data

US 2007/0274441 A1    Nov. 29, 2007

(30) Foreign Application Priority Data

May 26, 2006    (JP) ............................. 2006-146093

(51) Int. Cl.
*G01N 23/223*    (2006.01)
(52) U.S. Cl. ........................................ 378/44; 378/208
(58) Field of Classification Search ............ 378/44–50, 378/57, 58, 66, 68, 79, 208
See application file for complete search history.

(56) References Cited

U.S. PATENT DOCUMENTS

2002/0101957 A1* 8/2002 Feng ............................ 378/45
2004/0141585 A1* 7/2004 Proctor ......................... 378/57
2007/0269004 A1* 11/2007 Matoba et al. ................ 378/45
2008/0013681 A1* 1/2008 Fukai et al. ................... 378/44

FOREIGN PATENT DOCUMENTS

JP    2004-150990 A    5/2004

* cited by examiner

*Primary Examiner*—Hoon Song
(74) *Attorney, Agent, or Firm*—Brinks Hofer Gilson & Lione (57) ABSTRACT

To provide a fluorescent X-ray analysis apparatus, whereby a peak-back ratio is improved by effectively exciting a focused element and a detection limit of the focused element is improved by decreasing a scattered X-ray to be a background. A sample housing has one or more wall surfaces made of a material through which an X-ray transmits and an X-ray source is arranged so that a primary X-ray is irradiated on the wall surface. In addition, the sample housing is arranged so that a wall surface different from a wall surface on which the primary X-ray is irradiated is opposed to an X-ray detector incident window. Further, the primary X-ray from the X-ray source is arranged so as to be able to irradiate the wall surface of the sample housing to which the X-ray detector incident window is opposed. The sample housing has a shape extending in response to extension of a viewing filed that a detection element in the X-ray detector is seen from the X-ray detector incident window. In addition, on the wall of the sample housing, a metal for secondarily exciting the focused element is arranged on an area other than an area through which the primary X-ray transmits and an area where the fluorescent X-ray from the focused element passes to the detector.

11 Claims, 5 Drawing Sheets

FLUORESCENT X-RAY ANALYSIS APPARATUS

This application claims priority under 35 U.S.C. §119 to Japanese Patent Application No. JP2006-146093 filed May 26, 2006, the entire content of which is hereby incorporated by reference.

BACKGROUND OF THE INVENTION

1. Field of the Invention

The present invention relates to a fluorescent X-ray analysis apparatus for carrying out element analysis and composition analysis of a measured sample by irradiating a primary X-ray on the measured sample, inducing the fluorescent X-ray from the measured sample, and measuring energy of this fluorescent X-ray and intensity of the X-ray.

2. Description of the Related Art

Figure 10:
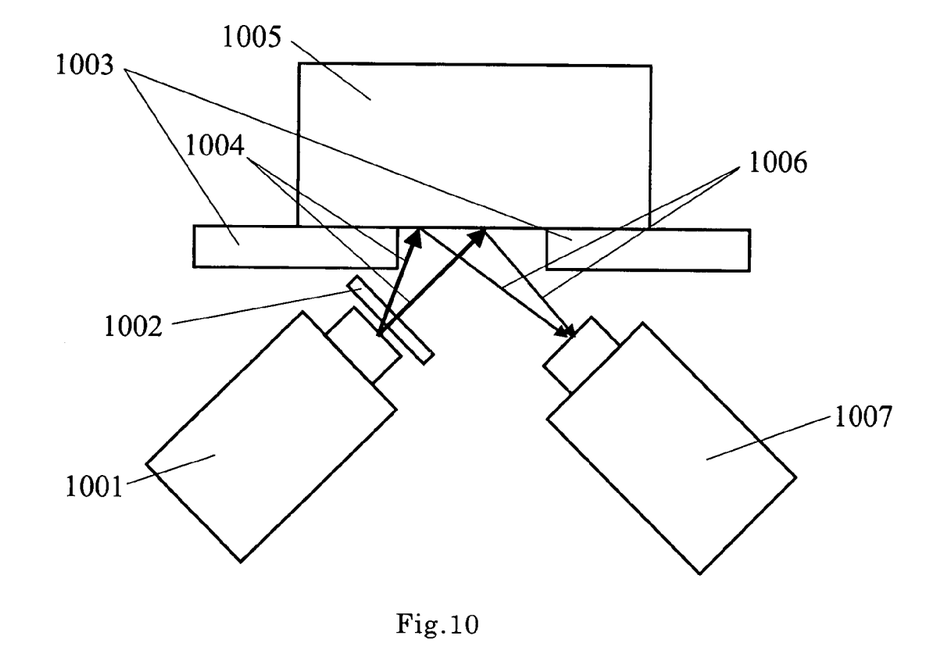
FIG. 10 is a pattern diagram of a conventional fluorescent C-ray analysis apparatus.

A conventional general fluorescent X-ray analysis apparatus will be described with reference to FIG. 10. Across a horizontal measured sample base 1003, a measured sample 1005 is arranged upward of the measured sample base 1003 and an X-ray source 1001, a primary filter 1002, and a detector 1007 are arranged downward of the measured sample base 1003. A reference numeral 1004 denotes a primary X-ray irradiated from the X-ray source 1001, and a reference numeral 1006 denotes a fluorescent X-ray generated when the measured sample 1005 is exited by the primary X-ray 1004. In this way, conventionally, the irradiated surface of the primary X-ray on the surface of the measured sample and the surface opposed to the detector on the surface of the measured sample are on the same plane.

In addition, it is general that a detection efficiency of the fluorescent X-ray from the focused element is improved by approaching the detector and the X-ray source to the measured sample as much as possible.

In addition, the apparatus having a primary filter in order to improve a ratio between a peak intensity of the fluorescent X-ray of the focused element and a background intensity mainly based on a scattered X-ray or the like (hereinafter, referred to as a peak-back ratio); the apparatus using a secondary target; and the apparatus using an optical device for making the X-ray into monochrome and focusing the X-rays are provided, however, all of them have the structure such that the detector is opposed to a point where the primary X-ray is irradiated (for example, refer to JP-A-2004-150990 (P.3 and FIG. 1)).

In the conventional fluorescent X-ray analysis, it is general to improve a peak-back ratio by using the primary filter when confirming a presence of a trace heavy metal such as cadmium contained in a light element major component which is composed of C, O, and H or the like and a density thereof. The present method is very useful, however, the primary X-ray is attenuated by inserting the primary filter and as a result, the intensity that the fluorescent X-ray of the trace heavy metal exited by the measured sample enters the detector is low.

Therefore, in order to make the intensity of the X-ray entering the detector stronger, the structure of approaching the detector and the X-ray source to the measured sample is applied. However, since both of the detector and the X-ray source are arranged so as to be opposed to the same plane on the surface of the measured sample, there is a limitation in a distance for approaching due to interruption of the both structural objects when approaching them to the measured sample. Therefore, it is general that a detection limit is several wt pap in measurement of several hundreds seconds when measuring a trace heavy metal in a light element.

In order to improve the detection limit of the trace heavy metal, a peak-back ratio is an important factor, however, volume of the intensity of the obtainable X-ray, namely, the sensitivity thereof is also an important factor. Hereinafter, a general formula of the detection limit is described. When the intensity of the X-ray is increased, in proportion to this, the background intensity and sensitivity are increased. In other words, from the following formula, the detection limit is improved (lowered) in inverse proportion to a root of the obtained intensity of the X-ray.

$$DL = \frac{3\sigma}{S}$$ [Formula 1]

$$\sigma = \sqrt{\frac{n_{BG}}{T_{LT}}},$$

$$S = \frac{n_P - n_{BG}}{C_i}$$

Here, DL denotes a Detection Limit, $n_p$ denotes peak intensity, $n_{BG}$ denotes background intensity, TLT denotes Live Time, and $C_i$ denotes density of a focused element.

SUMMARY OF THE INVENTION

The invention has been made taking the foregoing problems into consideration and an object thereof is to provide a fluorescent X-ray analysis apparatus, which efficiently excites a fluorescent X-ray of a focused element so as to prevent the intensity of the X-ray obtained by a detector from being lowered, effectively improve a peak-back ratio, and improves a detection limit.

In order to attain the above-described object, to increase a fluorescent the intensity of the X-ray from the focused element and to decrease a background which becomes a noise are considered.

Therefore, at first, a fluorescent X-ray analysis apparatus according to the invention may comprise a sample sealing member for housing a solid sample or a liquid sample made of a material through which an X-ray transmits; an X-ray source for generating a primary X-ray entering from the side wall of the sample sealing member in a radial pattern for X-irradiating the sample; and a detector, which is disposed being opposed to a bottom face of the sample sealing member and has an incident solid angle extending from an incident point to a detection element in a direction of a sample, for detecting a fluorescent X-ray to be generated from the sample given the primary X-ray; and the fluorescent X-ray analysis apparatus carries out analysis of an element of the sample from a spectrum of the detected fluorescent X-ray. As described above, in the conventional general fluorescent X-ray analysis apparatus, the irradiated surface of the primary X-ray on the surface of the measured sample and the surface seen by the detector on the surface of the measured sample are on the same plane, however, the invention is characterized in that the irradiated surface of the primary X-ray on the surface of the measured sample and the surface seen by the detector on the surface of the measured sample are different. Thus, the X-ray source can be more firmly attached to the sample sealing member, the primary X-ray can be put into the sample sealing member by making a radiation solid angle larger, and the primary X-ray can be irradiated to more samples. In addition, the detector can be more firmly attached to the sample as same as the X-ray source, so that an incident solid angle can be made larger and more fluorescent X-rays can be put in the sample sealing member. Therefore, the invention contributes to improvement of the detection limit. Here, the X-ray source other than the X-ray tube is also available if it irradiates a light in a radial pattern from the side of the sample sealing member toward the measured sample. For example, the secondary target and the optical device for making the X-ray into monochrome may be also available.

In addition, the sample sealing member has a taper shape which tapers off to the detector. Further, the taper shape is defined to extend from the bottom face of the sample sealing member in a direction opposed to the side where the detector is disposed in response to extension of the visual field of the detector. Thereby, the background which becomes the noise can be decreased and this is based on the following reason(s).

The background is formed with the primary X-ray to be irradiated from the X-ray source being scattered. A ratio that the primary X-ray of the light element is scattered is higher. In a relation between the X-ray energy and the intensity of the obtained X-ray (hereinafter, referred to as an energy spectrum), with the scattered X-ray having the same energy as the fluorescent energy from the focused element entering the detector, an adverse affect is given to detection of the focused element as a noise. Even when the fluorescent X-ray of the focused element is generated, the measured sample disposed in the field outside of a viewing field of the detector does not contribute to rising of the peak intensity of the fluorescent X-ray of the focused element since the X-ray cannot reach the detector. However, the measured sample disposed in this area scatters the primary X-ray and contributes to rising of the background. Thereby, only leaving the measured sample disposed in the area inside of the viewing field of the detector, no measured sample is left in the area outside of the viewing field of the detector, and this enable to decrease the scattered X-ray efficiently and to decrease the background without lowering the intensity of the fluorescent X-ray of the focused element.

Therefore, the sample sealing member has a taper shape extending from the bottom face opposed to the detector in a direction that the detector is seeing in response to extension of the visual field of the detector. Thereby, most of or all measured samples are housed in the area inside of the visual field of the detector and this makes it possible to decrease the background of the focused element.

Further, a metal wall is disposed, which generates a fluorescent X-ray best suitable for exciting the focused element on the side wall other than an incident part of the primary X-ray in the sample sealing member. Thereby, an excitation efficiency of the focused element is raised, so that it is possible to improve the peak-back ratio when the spectrum is obtained by the detector and to increase the intensity of the fluorescent X-ray of the focused element. Here, by making the shape of the sample sealing member into a taper shape extending from the wall opposed to the detector in a direction that the detector is seeing in response to extension of the visual field of the detector, the metal wall fluorescent X-ray as a noise generated from the metal surrounding the side wall of the sample sealing member is prevented from directly entering the detector. In addition, the metal wall has a convenient mechanism, which forms a part of the sample sealing member and is changed by rotation of the sample sealing member, so that space-saving of a driving part of the metal wall can be realized and it is possible to efficiently excite the focused element by approaching the metal wall for generating the metal wall fluorescent X-ray to the measured sample more.

On the other hand, selectively exciting the focused element between the X-ray source and the measured sample, the primary filter for lowering the background is mounted. Thereby, it is also possible to improve the peak-back ratio when the detector obtains spectrum. The primary filter has a convenient mechanism, which forms a part of the sample sealing member and is changed by rotation of the sample sealing member, so that space-saving of a driving part of the primary filter can be realized and it is possible to efficiently excite the focused element by approaching the X-ray source for generating the primary X-ray to the measured sample more.

In addition, mounting a secondary filter for selectively transmitting only the fluorescent X-ray from the focused element between the measured sample and the detector, the peak-back ratio when the spectrum is obtained by the detector can be improved and a saturated condition of the detector due to large amounts of the incident X-rays can be prevented. The secondary filter has a convenient mechanism, which forms a part of the sample sealing member and is changed by rotation of the sample sealing member, so that space-saving of a driving part of the secondary filter can be realized and it is possible to efficiently excite the focused element by approaching the detector to the measured sample more.

In addition, the sample sealing member can be made into a sample housing which is detachable and is formed in the same shape.

By using the above-described sample sealing member, the intensity of the X-ray from the focused element which can be obtained by the detector is increased, the background is decreased, the focused element contained in the light element is detected with a high sensitivity, and the detection limit can be improved.

The invention has the following advantages.

At first, by irradiating the primary X-ray from the sample sealing member to the measured sample in a radial pattern, the fluorescent X-ray generated from the entire cubic area where the primary X-ray irradiated area and the area seen by the detector are superimposed with each other is allowed to enter the detector, and thereby, it becomes possible to improve the obtained intensity of the X-ray.

Further, since the X-ray source and the detector can approach the sample sealing member without given the interference based on the structure of the apparatus as compared to the conventional case, generating the fluorescent X-ray from the sample with a high degree of density, it becomes possible to put these fluorescent X-rays in the detector with a broader angle. In addition, by making the sample sealing member into a taper in consideration of the viewing field of the detector, the background is decreased, namely, the peak-back ratio is improved.

From above, it becomes possible to improve the detection limit of the focused element. In addition, the measured time can be reduced at a detection level which could be realized by the conventional apparatus.

DETAILED DESCRIPTION OF THE INVENTION

The embodiment(s) of the invention will be described with reference to the drawings.

The invention is characterized in that an X-ray source is disposed being opposed to a side wall of a sample sealing member, an X-ray from the X-ray source emits from the side wall of the sample sealing member in a radial pattern so as to irradiate the measured sample, a detector for detecting a fluorescent X-ray generated from the sample receiving a primary X-ray is disposed being opposed to a bottom face of the sample sealing member, and an incident solid angle extending from an incident point toward a detection element in a direction of the sample.

Further, the invention is characterized in that a shape of the sealing member is formed in a taper which is gradually extended in response to extension of a viewing field of the detector.

Figure 2:
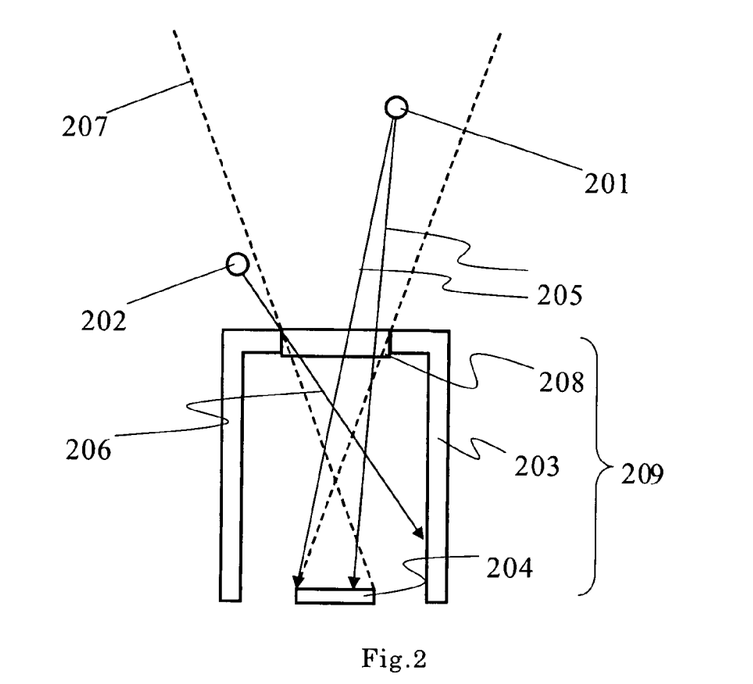
FIG. 2 is a pattern diagram with respect to a principle of the invention.

This point will be described in detail with reference to FIG. 2. FIG. 2 is a principle view showing the invention. A detector 209 is formed by a detector incident window 208, a detector wall 203, and a detection element 204 disposed inside of the detection wall. The detector wall 203 is made of a material which does not transmit the X-rays. A reference numeral 207 denotes a border line of a viewing field that the detection element 204 is seen from a detector incident window 208. Even if the measured sample 202 emits a fluorescent X-ray 206 of the focused element, a measured sample 202 disposed in the area outside of the viewing field of the detection element 204 through the detector wall 203 does not contribute to rising of a peak of the fluorescent X-ray of the focused element in an energy spectrum and the measured sample 202 disposed in the area scatters the primary X-ray so as to only contribute to rising of a background which becomes a noise because the X-ray does not reach the detection element 204. On the contrary, a fluorescent X-ray 205 irradiated from a measure sample 201 disposed in the area inside of the viewing field of the detection element 204 enters the detection element 204. Making the shape of the sample sealing member into a taper extending in response to extension of the viewing field through the detector wall 203 and making this into the same shape as the area inside of the viewing field of the detection element 204, only leaving the measured sample disposed in the area inside of the viewing field of the detection element 204, no measured sample is left in the area outside of the viewing field of the detection element 204, and this enable to decrease the scattered X-rays effectively and to decrease the background without lowering the intensity of the fluorescent X-rays of the focused element.

Figure 1:
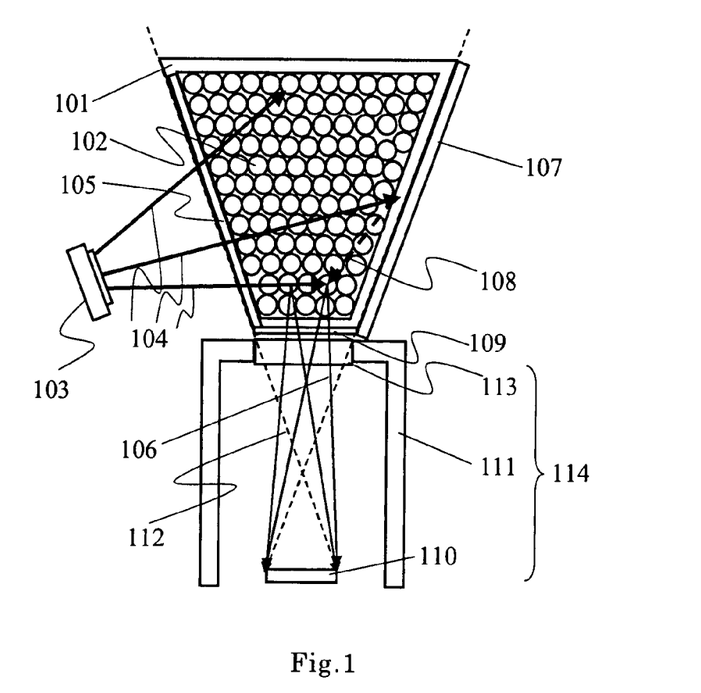
FIG. 1 is a pattern diagram of a part of a fluorescent X-ray analysis apparatus according to the invention.

FIG. 1 is a pattern diagram of an X-ray optical system of a fluorescent X-ray analysis apparatus according to the invention and shows a positional relation between a sample housing 101 as a sample sealing member, an X-ray source 103, a detector incident window 113, a detector wall 111, and a detection element 110 disposed inside of the detector wall. A detector 114 is formed by the detector incident window 113, a detector wall 111, and a detection element 110. The detector wall 111 is made by a material which does not transmit the X-rays. In FIG. 1, a grained measured sample 102 containing a focused element in a minute amount in FIG. 1 is filled in the sample housing 101, which is made of an organic material through which the X-rays can transmit relatively easily and a material such as aluminum, silicon, and magnesium. Here, by applying crush and compression process to the measured sample 102 and filling it in the sample housing 101 evenly with a high density, it is possible to generate the fluorescent X-ray effectively from the measured sample 102. Then, the measured sample 102 is set in an analysis apparatus together with the sample housing 101.

The invention is characterized in that the location where the primary X-ray 104 from the X-ray source 103 is irradiated and the location where the detector incident window 113 and the detection element 110 are facing are different on the sample housing 101. Therefore, approaching the X-ray source 103 and the detector incident window 113 to the sample housing 101 without receiving the interference of both of them, they can be firmly attached with each other. In FIG. 1, the detector incident window 113 is firmly attached to a bottom face 109 of the sample housing 101. In addition, the primary X-ray 104 from the X-ray source 103 is irradiated in the vicinity of the bottom face of the sample housing 101, to which the detector incident window 113 is firmly attached.

The primary X-ray 104 entered from a wall surface 105 of the sample housing 101 is irradiated to the measured sample 102. The focused element in the measured sample is excited by the primary X-ray to generate a fluorescent X-ray 106. A part of the fluorescent X-ray 106 generated from the focused element in a radial pattern transmits through the measured sample 102 and enters the detection element 110 through the detector incident window 113. A reference numeral 112 denotes a border line of a viewing field that the detection element 110 is seen from the detector incident window 113. In the detection element 110, the detector incident window 113 is firmly attached to the sample housing 101 and the distance between the detection element 110 and the sample housing 101 is made shorter, so that a solid angle from the measured sample 102 for the detection element 110 is made larger and the fluorescent X-ray 106 from the focused element enters the detection element 110 efficiently. This enables to improve the sensitivity.

Here, the X-ray source 103 for generating the primary X-ray 104 to be irradiated to the sample housing 101 other than the X-ray tube is also available if it irradiates a light in a radial pattern from the side of the sample sealing member toward the measured sample. For example, the secondary target and the optical device for making the X-rays into monochrome may be also available.

In addition, by mounting the primary filter 105 allowing the X-rays to selectively transmit therethrough for effectively exiting the focused element from the primary X-ray 104 on the wall surface which the primary X-ray 104 generated from the X-ray source 103 enters in the wall surface of the sample housing 101, the peak-back ratio of the focused element is improved when obtaining the X-rays by means of the detection element 110 and the saturated condition due to enormous amounts of the X-ray detection by the detection element 110 can be prevented. In addition, one or more primary filters are mounted in readiness for the case that there is a plurality of focused elements and there is provided a mechanism which can switch the primary filter 105 continuously by rotating the sample housing 101 without a complex mechanism.

Figure 7:
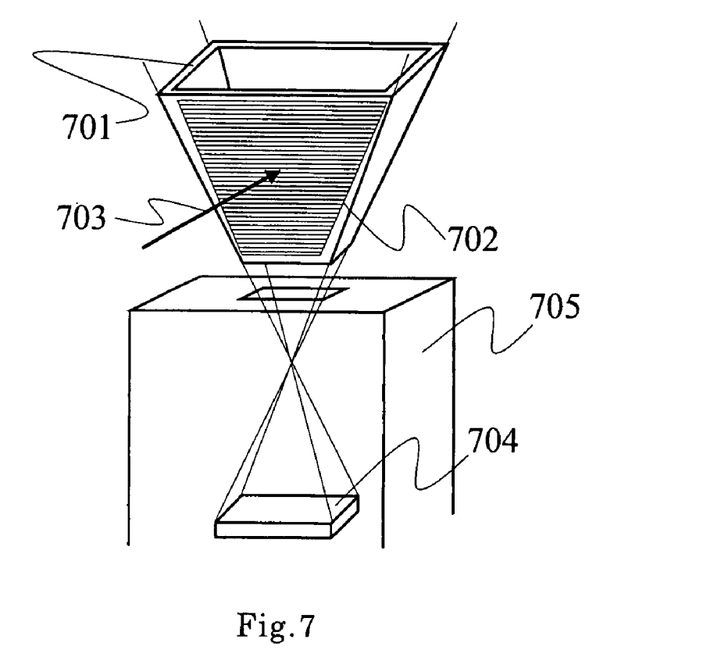
FIG. 7 is a pattern diagram of a sample housing, of which wall is partially formed by a plurality of primary filters.

Specifically, the present embodiment will be described with reference to FIG. 7. FIG. 7 shows the mode that a primary X-ray 703 enters a primary filter 702 from a part of the wall surface of a sample housing 701. A reference numeral 704 denotes a detection element disposed inside of a detector wall 705. One or more primary filters 702 are mounted on the wall surface of the sample housing 701 and only by rotating the sample housing 701, it is possible to change the primary filter. Thus, a space of a driving part of the primary filter can be saved and the X-ray source can be approached to the measured sample more so as to be able to excite the focused element.

On the other hand, on the wall of the sample housing 101, a metal wall for secondary excitation 107 for generating a fluorescent X-ray best suitable for exciting the focused element on the side wall other than an incident part of the primary X-ray 104. Most of the primary X-rays 104 entered the sample housing 101 transmit through the relatively light measured samples 102 without interaction with each other.

The primary X-rays 104 transmitted through the measured samples 102 may excite the metal wall for secondary excitation 107 and as a result, a metal wall fluorescent X-ray 108 best suitable for exciting the focused element in a minute amount is generated. This metal wall fluorescent X-ray 108 effectively excites the focused element in the measured sample 102 and improves the peak-back ratio of the focused element in the energy spectrum when the X-rays are obtained by the detection element 110.

Further, since the sample housing 101 has a taper shape similar to the viewing field of the detection element 110, it is possible to prevent the metal wall fluorescent X-ray 108 generated from the metal wall for secondary excitation 107 from directly reaching the detection element 110.

Figure 8:
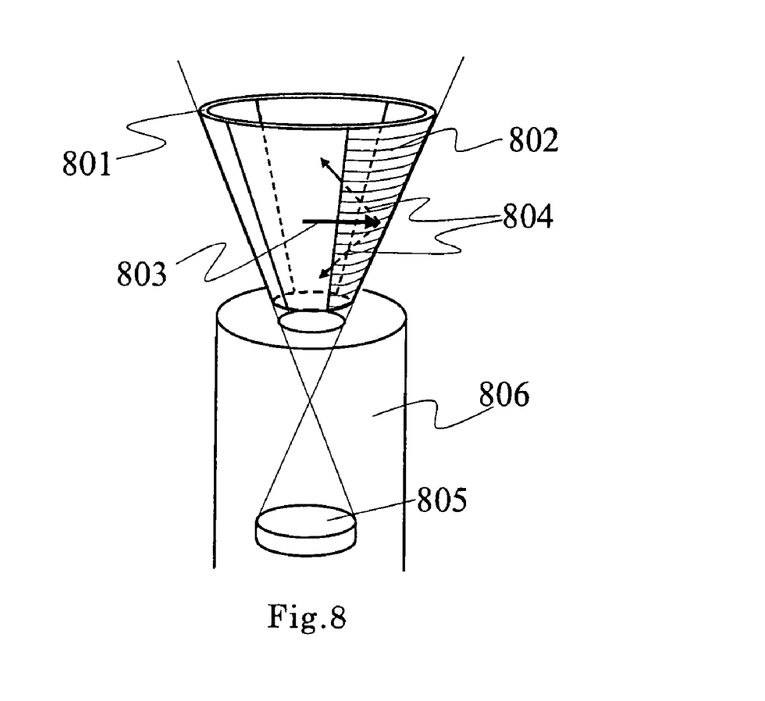
FIG. 8 is a pattern diagram of a sample housing, of which wall is partially formed by a plurality of metals for secondary excitation.

FIG. 8 shows the mode that a primary X-ray 803 transmits through a measured sample in a sample housing 801 so as to excite a metal wall 802 and generate a metal wall fluorescent-X ray 804. A reference numeral 805 denotes a detection element disposed inside of a detector wall 806. One or more metal walls 802 are mounted on the sample housing 801 and the metal has a mechanism which can change the metal wall 802 continuously by rotating the sample housing 801 without a complex mechanism.

In addition, by mounting a secondary filter for allowing only the fluorescent X-ray 106 from the focused element to selectively transmit there through on the wall surface 109 being opposed to the detector incident window 113 in the wall surface of the sample housing 101, the peak-back ratio when the X-rays are obtained by the detection element 110 can be improved and a saturated condition due to enormous amounts of the incident X-rays can be prevented.

Figure 9:
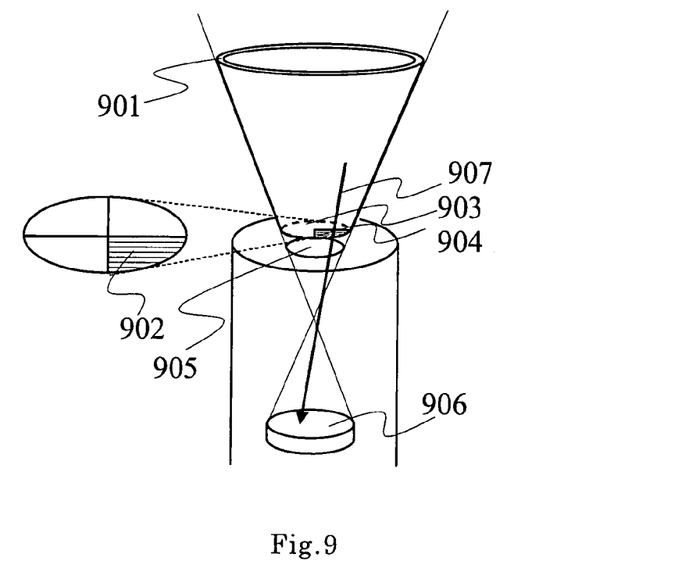
FIG. 9 is a pattern diagram of a sample housing, of which wall is partially formed by a plurality of secondary filters.

FIG. 9 shows the mode that one or more secondary filters 902 are mounted on the bottom face of a sample housing 901. A portion 903 is made of a material not allowing the X-rays to transmit there through and only allows an X-ray 907 entered a portion 904 to be transmitted to the outside of the sample housing 901. Then, the X-ray 907 reaches a detection element 906 through a detector incident window 905 and there is provided a mechanism which can switch the secondary filter continuously by rotating the sample housing 901 without a complex mechanism.

Even when there is not provided the sample housing 101 shown in FIG. 1, by making the shape of the measured sample housing similar to that of the sample housing 101 and filling the measured sample in the measured sample housing, an advantage of the invention can be realized.

Even when there is not provided any one or plurality of the first filter 105, the metal wall for secondary excitation 107, and the secondary filter arranged on the wall surface 109 of the sample housing 101, it is possible to realize a part of the advantage according to the invention.

A part of the external wall of the sample housing 101 is formed by any one or plurality of the primary filter 105, the metal wall for secondary excitation 107, and the secondary filter arranged on the wall surface 109 of the sample housing 101, it is possible to allow the X-ray source 103 and the detection element 110 to approach the sample housing 101 the most. As a result, it is possible to maximize the advantage of the invention.

The invention is characterized in that the sample housing 101 has a taper shape gradually extending in response to extension of a viewing field that the detection element 110 is seen from the detector incident window 113.

Therefore, according to the present embodiment, the X-ray source 103 is arranged on the side wall of the sample housing 101 and the detector incident window 113 is arranged on the bottom face wall of the sample housing 101. However, if the condition that the location where the primary X-ray 104 is irradiated on the wall face of the sample housing 101 and the location where the detection element 110 is seen from the detector incident window 113 are different is met, it may be also possible to arrange the X-ray source 103 on the surface different from the side wall of the sample housing 101 or it may be also possible to arrange the detector incident window 113 on the surface different from the bottom face.

Figure 3:
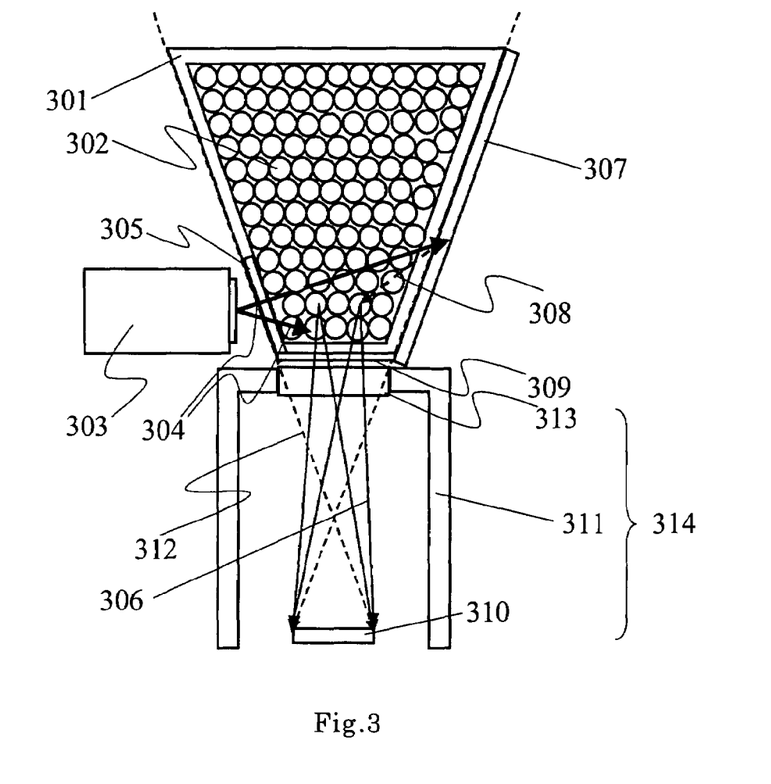
FIG. 3 is a pattern diagram of a part of a fluorescent X-ray analysis apparatus in the case that sample housing is formed by a primary filter, a metal wall for secondary excitation, and a secondary filter.

Hereinafter, citing analysis of Cd (cadmium) in a cereal as an example, an embodiment of the invention will be described. Here, the X-ray tube as the X-ray source, the X-ray detector as the detector, and the sample housing as the sample sealing member are used. FIG. 3 shows the mode that a cereal 302 containing Cd is filled in a sample housing 301 and an X-ray tube 303, and an X-ray detector 314 formed by an X-ray detector incident window 313, an X-ray detector wall 311, and an X-ray detection element 310 are arranged for a sample housing 301. Here, the X-ray detector wall 311 is made of a material which does not transmits the X-rays.

Figure 4:
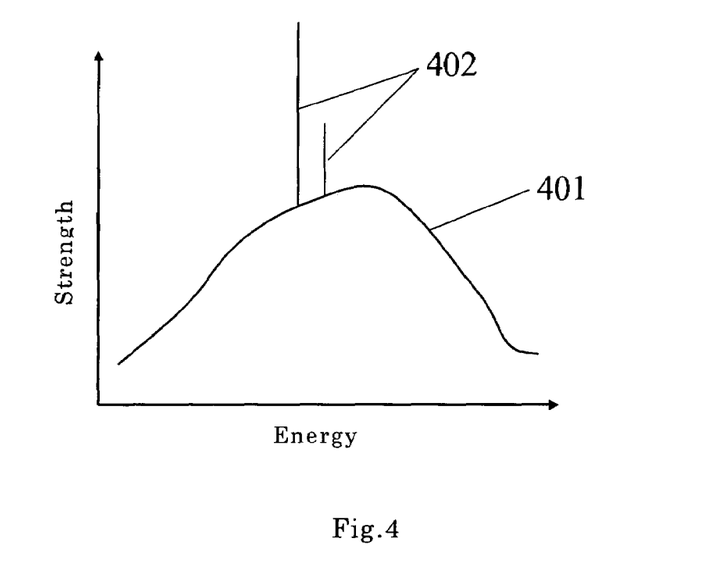
FIG. 4 is a pattern diagram of an X-ray energy spectrum from an X-ray source.

An energy spectrum of a primary X-ray 304 to be radiated from the X-ray tube 303 is as shown in FIG. 4. The energy spectrum of FIG. 4 is formed by a continuous X-ray 401 to be radiated from a target of the X-ray tube and a property X-ray 402. The primary X-ray 304 enters from the external wall of the sample housing 301 to be irradiated to the cereal 302. Here, in order to excite Cd in the cereal 302, energy higher than an absorption end of Cd should be irradiated. Therefore, an X-ray of a lower energy than the absorption end (26.7 keV) of Cd is absorbed on the external wall surface opposed to the X-ray tube 303 of the sample housing 301 and a primary filter 305 allowing the higher energy than the absorption end of Cd to transmit there through is mounted, and a quality of radiation of the X-ray is changed so as to be able to efficiently excite Cd.

Figure 5:
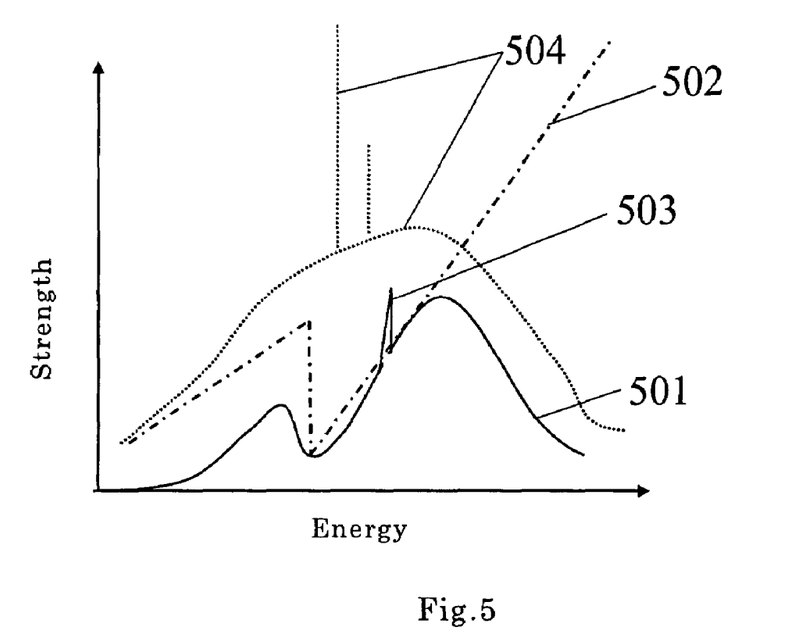
FIG. 5 is a pattern diagram of an X-ray energy spectrum after transmitting through the primary filter.

A reference numeral 504 of FIG. 5 denotes an energy spectrum of the primary X-ray 304 after transmitting through the primary filter 305 and a reference numeral 502 represents an X-ray transmission ratio of the primary filter. A radiation spectrum 503 is generated by exciting the focus element in the measured sample by means of the primary X-ray. A reference numeral 501 denotes a spectrum of the X-rays entered the X-ray detector after transmitting through the primary filter. Due to the effect of the primary filter, the peak of the focus element can be confirmed. Some of the primary X-rays 304 entered from the external wall of the sample housing 301 may interact with the cereal 302 in the sample housing 301 and others thereof may transmit through the primary filter 305 without interacting with the cereal 302. Further, some of the primary X-rays interacting with the cereal 302 may emit an X-ray which is peculiar to a constitutional element of the cereal 302 in the sample housing 301, namely, a fluorescent X-ray in a radial pattern and others thereof may scatter the primary X-rays in a radial pattern to emit the scattered X-rays.

In order to detect Cd in the cereal 302 with a high sensitivity and improve (lower) the detection limit of Cd, it is necessary to decrease the scattered X-rays to be a background noise as much as possible and increase the net amount of the Cd fluorescent X-rays from the cereal 302 by means of the X-ray detector. In order to realize the above-described two points, the shape of the sample housing 301 is determined as follows.

In other words, the sample housing 301 is formed in a taper shape, which is the same shape as the viewing field of the X-ray detector, namely, the area inside of the viewing field that an X-ray detection element 310 is seen from an X-ray detector incident window 313, and gradually expands in response to expansion of the viewing field. A reference numeral 312 denotes a border line of the viewing field that the X-ray detection element 310 is seen from an X-ray detector incident window 313. A reason why the sample housing 301 is formed in a taper shape is that a fluorescent X-ray 306 from the area outside of the viewing field of the X-ray detection element 310 cannot directly enter the X-ray detection element 310 and it is only necessary for the cereal 302 to be located in the area inside of the viewing field of the X-ray detection element 310 where the fluorescent X-rays of Cd directly enter the X-ray detection element 310. Then, since the scattered X-ray as the background noise is increased depending on the amount of the cereal 302, by forming the sample housing into a taper shape, it is possible to increase the scattered X-ray to be a background noise without providing the cereal 302 in the area outside of the viewing field of the X-ray detection element 310 which does not contribute to detection of the Cd fluorescent X-rays.

The X-ray tube 303 is arranged near the wall surface 305 of the sample housing 301 or so as to be firmly attached to the wall surface 305 of the sample housing 301. On the wall surface 305, the primary filter is mounted.

In addition, on the wall surface other than the incident surface of the primary X-ray 304 on the side wall surface of the sample housing 301, a metal wall for secondary excitation 307 for emitting the fluorescent X-rays having energy slightly higher than the absorption end energy of Cd, for example, tellurium (Te) or the like is mounted. Thereby, radiating fluorescent X-rays 308 from the metal wall for secondary excitation 307 by the X-rays transmitting through without interacting with the cereal 302 in the primary X-rays 304 emitted to the sample housing 301 and secondarily exciting Cd in the cereal 302, enable to increase the amounts of the fluorescent X-rays of Cd. Then, by defining the sample housing into a taper shape as described above, this also serves to prevent the fluorescent X-rays 308 emitted from the metal wall for secondary excitation 307 to be a background noise from directly entering the X-ray detection element 310. In many cases, the metal wall is arranged between the X-ray source and the measured sample also in the conventional fluorescent X-rays, however, the invention is characterized in that the measured sample is arranged between the X-ray source and the metal wall.

The fluorescent X-rays and the scattered X-rays radiated from the cereal 302 may emit the X-ray detection element 310. The X-ray detection element 310 has a limitation in countable number per unit time, so that when the X-rays more than the limitation number enters, the number of the X-rays which can be counted in practice is decreased and this deteriorates the detection efficiency. Therefore, by mounting a secondary filter 309 such as Ag having an absorption end of energy slightly higher than the fluorescent X-rays of Cd on the wall surface opposed to an X-ray detector incident window 313 on the wall surface of the sample housing 301, the fluorescent X-rays of Cd are not absorbed much and by absorbing the scattered X-rays having higher energy than the fluorescent X-rays of Cd more, saturation of counting is prevented.

Figure 6:
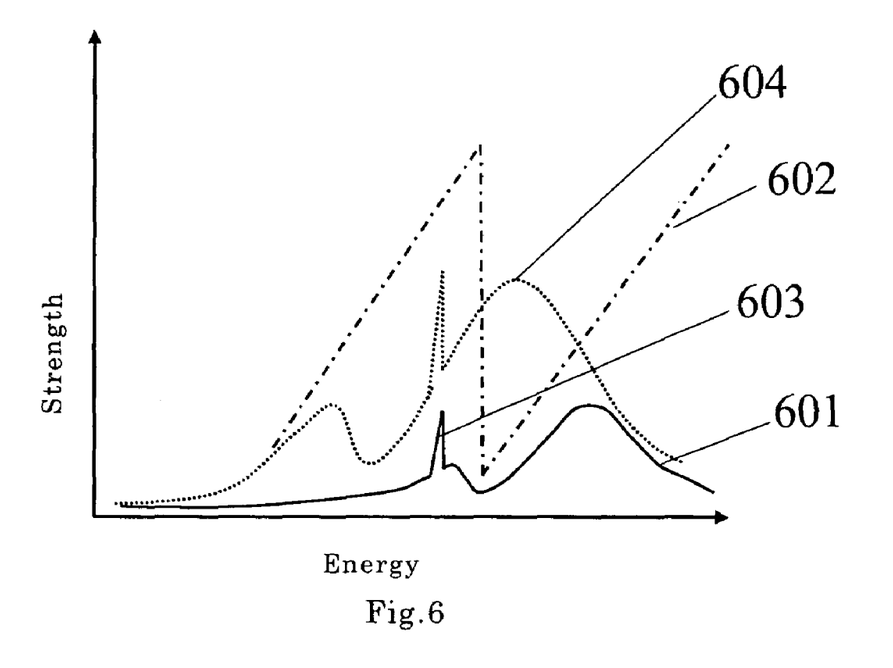
FIG. 6 is a pattern diagram of an X-ray energy spectrum after transmitting through the secondary filter.

A reference numeral 604 of FIG. 6 shows the energy spectrum of the fluorescent X-ray 306 of the scattered X-ray and the focused element at the X-ray detection element 310 when the secondary filter 309 is not used. By mounting the secondary filter, the energy spectrum of the fluorescent X-ray 306 of the scattered X-ray and the focused element after transmitting through the secondary filter 309 is represented by 601. A reference numeral 602 represents an X-ray transmission ratio of the secondary filter. Thus, decreasing the background around the focused element by means of the secondary filter, it is possible to improve a ratio between a peak 603 of the focused element and a background (a peak back ratio).

What is claimed is:

1. A fluorescent X-ray analysis apparatus comprising:
    a sample container configured to store a quantity of sample and comprising an end wall made at least in part X-ray transmissive and a side wall tapered such that it becomes narrower towards the end wall;
    at least one X-ray source located in close proximity to the side wall to interrogate the quantity of sample with an X-ray through the side wall; and
    at least one X-ray detector configured to detect, through the end wall of the sample container, a fluorescent X-ray excited out from the quantity of sample, wherein the at least one X-ray detector comprises a periphery configured and placed so as to generally coincide with a perimeter defined by an imaginary extension of the tapered side wall from the end wall.

2. A fluorescent X-ray analysis apparatus according to claim 1, wherein the at least one X-ray detector is located below a focal point of the imaginary extension.

3. A fluorescent X-ray analysis apparatus according to claim 1, wherein the side wall is made at least in part X-ray transmissive.

4. A fluorescent X-ray analysis apparatus according to claim 1, wherein the side wall has a circular cross section.

5. A fluorescent X-ray analysis apparatus according to claim 1, wherein the side wall has a polygonal cross section.

6. A fluorescent X-ray analysis apparatus according to claim 1, wherein the at least one X-ray source is arranged such that it irradiates the end wall of the sample container with the X-ray.

7. A fluorescent X-ray analysis apparatus according to claim 1, wherein the side wall comprises at least one primary filter configured to pass through the X-ray within a different wavelength range.

8. A fluorescent X-ray analysis apparatus according to claim 7, wherein the at least one X-ray source is movable relative to the sample container such that the at least one X-ray source irradiates the quantity of sample selectively through the at least one primary filter.

9. A fluorescent X-ray analysis apparatus according to claim 1, wherein the end wall comprises at least one secondary filter configured to pass though the X-ray within a different wavelength range.

10. A fluorescent X-ray analysis apparatus according to claim 9, wherein the end wall is movable relative to the at least one secondary filter such that the at least one X-ray detector receives the florescent X-ray selectively through the at least one secondary filter.

11. A fluorescent X-ray analysis apparatus according to claim 1, wherein the side wall is made at least in part of at least one material which, excited by the X-ray, generates a different secondary X-ray sufficient to excite the fluorescent X-ray out from the quantity of sample.

* * * * *